United States Patent [19]
Karl

[11] Patent Number: 5,804,450
[45] Date of Patent: Sep. 8, 1998

[54] METHOD AND REAGENT FOR THE SPECIFIC DETERMINATION OF LDL IN SERUM SAMPLES

[75] Inventor: Johann Karl, Peissenberg, Germany

[73] Assignee: Boehringer Mannheim GmbH, Mannheim, Germany

[21] Appl. No.: 604,083

[22] Filed: Feb. 20, 1996

[30] Foreign Application Priority Data

Feb. 21, 1995 [DE] Germany ............... 195 05 894.1

[51] Int. Cl.⁶ .................................. G01N 33/92
[52] U.S. Cl. .............. 436/71; 436/13; 436/815; 436/825
[58] Field of Search ................. 435/11; 436/815, 436/825, 71, 13

[56] References Cited

U.S. PATENT DOCUMENTS 5,411,870  5/1995  Law et al. .................. 436/71

FOREIGN PATENT DOCUMENTS 76211  4/1983  European Pat. Off. .
4223355  1/1994  Germany .

*Primary Examiner*—Mary E. Ceperley
*Attorney, Agent, or Firm*—Felfe & Lynch

[57] ABSTRACT

The invention relates to a method and reagent for the specific determination of the LDL fraction in the presence of other serum lipoproteins by adding a water soluble polymeric LDL-aggregating agent and a zwitterionic and/or non-ionic detergent. The LDL aggregate is determined in a direct turbidimetric measurement. Preferred LDL-aggregating agents are polyanions having a branched structure with acid groups, particularly branched alkane sulfonic acid groups as side branches. Preferred detergents are those known as "Zwittergent".

14 Claims, 3 Drawing Sheets

METHOD AND REAGENT FOR THE SPECIFIC DETERMINATION OF LDL IN SERUM SAMPLES

The invention addresses a method for the specific determination of LDL in biological liquids in the presence of an LDL precipitating agent and/or a water-soluble polymer, especially a polyanion and a detergent and/or a detergent mixture. The invention also relates to a reagent suitable therefor which brings about the advantage of a significantly reduced VLDL interference. The polymers are in particular those with a branched structure, where the side branches have acid groups, especially branched alkane sulphonic groups.

The determination of the LDL level in plasma and especially in serum has gained high clinical importance: up to the 80% of the total cholesterol contents are transported in the form of so-called low-density lipoproteins (LDL or β-fraction) and are thus part of those particles which today are considered most significant atherogenic components in the lipid metabolism. Moreover, it is known that elevated plasma LDL concentrations can have a direct endothelial damaging effect which is comparable to other noxae such as hypertension, hyperinsulinemia or endotoxins. It is also known that the cholesterol deposited in an atherosclerotic plaque was originally also present in the plasma in the form of LDL cholesterol.

Today, there are several methods available for the quantitative determination of LDL or β-cholesterol in plasma and especially in serum (Mills, G. L., Lane, P. A., Weech, P. K.: A guidebook to lipoprotein technique. Elsevier, Amsterdam, 1984; Cremer, P. and Seidel, D.: Dtsch. Gesell. Klin. Chem. Mittl. 21, 1990, 215–232).

An essential difference is made between differentiating techniques such as ultracentrifugation and electrophoresis, on the one hand, and precipitation techniques on the other hand. The former require expensive instrumentation and are very time-consuming. They are therefore primarily used as reference and confirmation tests. Precipitation with high-molecular, mostly negatively charged substances is today a routine method in the laboratory. Dextrane sulfate, polyvinyl sulfate, polycyclic surface-active anions or heparin are used in particular as LDL precipitation reagents in today's clinical diagnostics. However, these methods have one disadvantage. The precipitation with heparin in an acid medium or with polycyclic anions in serum samples with preceding or existing lipolytic activity leads to falsely elevated results for LDL cholesterol. When using dextrane sulfate or polyvinyl sulfate (PVS), which today are considered the reagents of choice as they show the highest precision for LDL determinations, the values found in serum samples with preceding or existing lipolytic activity are falsely depressed. Moreover, dextrane sulfate-containing precipitation reagents also lead to falsely depressed results when high levels of free fatty acids or triglycerides are present in the sample to be assayed. Interference in triglyceride-rich samples is primarily caused by the presence of high VLDL concentrations. This is even more so the case in patients under heparin therapy. Another disadvantage that is common to all precipitation methods is that in addition to LDL, the LDL-like lipoprotein Lp(a) is also subject to precipitation. The methods are, hence, not entirely LDL-specific.

DE 42 23 355 describes a method for the specific determination of LDL using polymers having certain alkane sulphonic acid groups. However, this method only partially satisfies today's demands, particularly with respect to samples with a high VLDL percentage.

It was, hence, an object of the invention to provide a method for the specific determination of LDL that is easy and fast and does not exhibit interference by lipoprotein particles, particularly VLDL or increased concentrations of triglycerides or free fatty acids or heparinized samples.

This object is accomplished in that an LDL-precipitating agent or a water-soluble polymer, for example, one containing anionic side branches and a detergent or a detergent mixture is added to the samples to be assayed. Subsequently, the contents of the forming LDL-specific aggregate (agglutinate) is directly determined in a turbidimetric measurement. The VLDL interference can also be reduced in conventional routine methods with dextrane or PVS as a precipitating agent in that the detergent or detergent mixture in accordance with the invention is added.

Possible water-soluble polymers are those having anionic side groups according to DE 42 23 355 which are derived from acrylic acid ester monomers, but it is also possible to use dextrane sulfate and heparin. Particularly preferred are compounds of the general formula (I):

wherein $R^1$ is hydrogen or a lower hydrocarbon residue, preferably a methyl group, X is an oxygen atom or an NH group, A is a linear branched hydrocarbon chain consisting of 2 to 10 C atoms, with branched chains being preferred, and Z is a

Homopolymers of 2-acrylamido-2-methyl-1-propane sulphonic acid, 2-acrylic amidoglycollic acid and/or copolymers of said monomers have proven to be particularly suitable.

The polymers of the anionic side chains have a preferred molecular weight of $2 \times 10^4$ to $5 \times 10^6$ Dalton, particularly preferred about $5 \times 10^5$ Dalton (gel permeation chromatography).

These anionic polymers can be prepared by means of methods that are known to the expert, including solution, suspension or emulsion polymerization (Meth. d. Organ. Chemie (Houben-Weyl), Vol. E 20, Makrom. Stofte, Thieme Verlag, Stuttgart, 1987). Solvent polymerization as described in Polymer 31 (1990), 1269–1267 (Huglin and Rego) is particularly preferred. The polymerization can be accelerated with the aid of conventional initiators, especially peroxides, persulfates or persulfates/bisulfits or the corresponding azo compounds that are present in aqueous systems in the form of free radicals. This is also known to the expert.

The concentration of one or several of the branched polyanions ranges between 0.001 and 5.0 mg/ml and preferably ranges between 0.005 and 1.0 mg/ml. A particularly suitable range is one between 0.01 and 0.1 mg/ml.

The detergents to be added in accordance with the invention are particularly those with a zwitterionic character of the general formula (II):

wherein x is a number between 1 and 20, and y is a number between 0 and 8, $R^1$ is hydrogen, a cholamido group or a mono- or diglyceride group bound via phosphate residue, $R^2$ is hydrogen, a hydroxyl group or an oxyanion, an acid residue, a hydroxyalkyl sulphonic acid group or a carboxyl group.

Preferred detergents are those where x is an odd number between 11 and 17, y is a number between 1 and 3 and/or $R^2$ is a sulphonic acid residue, a hydroxyethyl sulphonic acid residue, a hydroxypropyl sulphonic acid residue or a carboxyl residue, or $R^1$ is hydrogen, a steroid frame, a lecithin or a lysolecithin residue.

Particularly suitable detergents are the following: N-dodecyl-N,N-dimethylammonio-3-propane sulfate or the corresponding N-tetradecyl or N-hexadecyl compound (type "Zwittergent": Zwittergent 3-14, 3-16), N-dodecyl-N,N-dimethyl-glycine (Empigen BB®), aminoxide, CHAPS, CHAPSO and α-lecithin (α-phosphatidylcholin) or α-lysolecithin (α-lysophosphatidylcholin). All detergents are commercially available.

The zwitterionic detergents are used either solely or in combination with a non-ionic detergent such as Pluronic F68 and/or Tween 20.

Generally, it is possible to use buffer substances for the method of determination of the invention provided their buffering capacity is in weakly acidic, neutral, or weakly alkaline pH range. Particularly suitable buffer substances are sodium acetate and so-called Good buffers, such as TRIS.HCl, BIS-TRIS methane, MES or imidazole. The pH value for the determination when using these buffers, preferably ranges between pH 5 and 9, particularly preferred between 7.0 and 8.0, a particularly suitable range is one between 7.3 and 7.7. The concentration of the buffer should range between 0.001 and 0.2 mol/l. A particularly suitable concentration range is one between 0.005 and 0.07 mol/l.

A preferred embodiment employs a TRIS.HCl buffer, a bis[2-hydroxyethyl]imino-tris [hydroxymethyl]methane (bis-TRIS) buffer, an MES or an imidazole buffer in the presence of 2-valent metal ions. The concentration of the buffer ranges between 0.001 and 0.2 mol/l, the concentration of the metal salts between 0.001 and 0.20 mol/l and the pH value ranges between 5.5 and 9.0. In particularly preferred embodiment, the concentration of the buffer ranges between 0.005 and 0.07 mol/l, the concentration of the metal salts between 0.01 and 0.03 mol/l, and the pH value ranges between 7.0 and 8.0. Generally, it is possible to employ all salts of known 2-valent metal ions. Particularly preferred are $Mg^{2+}$, $Ca^{2+}$, $Mn^{2+}$, and $Cu^{2+}$. $Mg^{2+}$ and $Ca^{2+}$ have proven to be particularly suitable. The polyanion concentration should be selected as indicted above.

Another subject matter of the invention is a reagent containing a water-soluble polymer and a zwitterionic and/or a non-ionic detergent and a substance buffering in a pH range between 5 and 9. The amount of polymers used ranges between approximately 0.005 and 1.0 mg/ml of reagent solution; particularly preferred are poly-(2-acrylamido-2-methyl-1-propane sulphonic acid) (PAMPS), polyacrylic acid-(2-phospho-1,1-dimethyl-ethylamide) (PAP), poly-2-acrylamido-glycollic acid (PAAG), poly-(2-acrylamido-2-methyl-1-propane sulphonic acid-CO-2-acrylamido-glycollic acid) [P(AMPS-AAG)] and/or corresponding polymers and/or corresponding poly(meth)acrylic acidic ester or even dextrane sulfate, polyvinyl sulfate or heparin in a concentration range between 0.02 and 0.04 mg/ml, particularly preferred in a concentration range of 0.02 to 0.04 mg/ml.

The amount of detergent to be added depends on the type of detergent used. The efficiency of the VLDL interference reduction in case of detergents with a shorter chain length (x, y<4) is achieved only when higher concentrations are used. The addition of a zwitterionic detergent at a concentration of approximately 0.002 to 1.0% (w/v) has proven to be particularly suitable in the method.

Particularly suitable buffer substances are sodium acetate, TRIS.HCl, BIS-TRIS, MES, and imidazole. The preferred concentration of the buffer ranges between 0.001 and 0.2 mol/l.

The given concentrations are final concentrations, i.e. the concentration found in the reaction mixture.

The pH value range of the reagent for the determination of LDL is between 5.0 and 9.0, preferably between pH 7.0 and 8.0 or between pH 7.3 and 7.7. The temperature for the determination may vary between 10° and 40° C., preferred is a temperature of approximately 37° C.

The ratio of sample volume to be assayed to reagent solution is variable. Ratios between 1:6 and 1:100 have proven to be suitable. It is preferred to mix approximately 5 parts of the serum sample (e.g. 5 μl) with 300 parts reagent solution (e.g. 300 μl). Samples are in particular biological liquids such as serum, plasma, or urine.

Moreover, it has proven to be advantageous to first prepare two separate reagent solutions; one containing a 2-valent metal ion and a second a water-soluble polymer aggregation agent. A zwitterionic and/or a non-ionic detergent is added either to the first reagent to which then the sample is added or to both reagents.

As compared to other known methods, the LDL-specific aggregation or agglutination that was triggered with an LDL precipitating agent such as dextrane sulfate, polyvinyl sulfate, or heparin and preferably with an anionic polymer (PAMPS) and one or several of the detergents in accordance with the invention has the following advantages:

1. In addition to LDL, the apoprotein B-containing lipoproteins such as very-low density lipoproteins (VLDL), Lp(a) and/or chylomicrons do not interact with the combination in accordance with the invention either, and are thus not measured.
2. High triglyceride concentrations do not negatively affect the result.
3. The determination is carried out rapidly, without sample pretreatment (approximately 1 to 10 min).
4. Forming aggregate is present in a very stable condition and can be directly measured and reproduced.
5. The determination of LDL cholesterol is linear over a very broad measuring range (50 to 350 mg/dl LDL cholesterol).

The method and/or reagent of the invention leads to an absolutely specific agglutination of LDL particles within 1 to 5 min. There is no interference by increased triglyceride concentrations, and a preceding separation of other lipoprotein fractions is not required either. The assay can hence be run on analyzers or simple photometers (turbidimetric) for the determination of the LDL concentration or the LDL cholesterol which is desirable for routine work. Moreover, it is also possible to determine the apoprotein B-100 and/or other molecular components of the LDL particle contained in the LDL agglutinate.

The broad measuring range where the method of the invention exhibits a linear measuring signal covers the diagnostically relevant range, especially the one of elevated LDL values (>190 mg/dl) with the advantage of requiring only one-point calibration. Because of the elevated linear range, it is also possible to have a more precise quantitative monitoring of elevated LDL levels without requiring expensive confirmation procedures such as lipoprotein electrophoresis or ultracentrifugation.

The method and reagent in accordance with the invention agglutinates LDL but not the additional LDL-similar Lp(a). This finding is surprising as all known LDL precipitation reagents also precipitate at least partially the Lp(a) fraction. It is, hence, possible with the present invention to also determine the Lp(a) fraction in a simple manner by reductively cleaving of the Lp(a) portion of the Lp(a) particle which is bound via a disulfide bridge subsequent to the LDL agglutination and determination in accordance with the invention. By obtaining the difference, it is possible to determine the contents of lipoprotein(a).

Moreover, note that despite the present teaching that the addition of detergents greatly affects the LDL precipitation, it was surprisingly possible to prevent the simultaneous precipitation of VLDL by adding zwitterionic detergents especially Zwittergent or mixtures of non-ionic detergents without affecting the specific precipitation of LDL. It is particularly critical to determine the optimal concentration of the detergent in the reaction mixture. If a concentration is used that is too low, the reduction of the interference is almost non-existent, while too high detergent concentrations prevent the simultaneous precipitation of VLDL but also reduce the complete precipitation of the LDL particles. With the method and reagent of the invention, it is possible to have an interference-free LDL determination up to approximately 130 mg/dl VLDL contents. This corresponds to a triglyceride contents of approximately 800 mg/dl, while routine methods such as dextrane sulfate precipitation already shows significant interference beginning at 400 mg/dl of triglycerides.

It is also possible to carry the method of the invention out on test strips or similar matrices, provided the individual reaction components are impregnated on or in a carrier material or covalently bound. Possible carrier material is absorbent or film-forming carrier material with the capability to swell as it is commonly used for test strips, e.g. paper or similar fleece material such as tea bag paper. The reaction components can be distributed on several carriers that are in contact with one another or serve as carriers themselves. Covalently bound polyanions (e.g. PAMPS) allow the complete, selective separation of LDL on a test strip. The LDL cholesterol value can be determined by measuring the cholesterol contents of the non-bound lipoprotein particles and obtaining the difference with total cholesterol contents.

Abbreviations used
CHAPS=[3-(3-cholanidopropyl)-dimethylammonio]-1-propane sulfate
CHAPSO=[3-(3-cholanidopropyl)-dimethylammonio]-2-hydroxy-1-propane sulfate
MES=2-N-morpholino-ethane sulfonic acid

-☐- without detergent
-x- 0.005% Zwittergent 3-14

The following examples explain the invention in greater detail:

EXAMPLE 1

Effect of the Zwittergent Concentration on the Reduction of VLDL Interference in a homogenous LDL Test Reagent solution 1

10 mM Bis-Tris Methane, pH 7,5

12mM MGCl2 x% Zwittergent 3-14 (=N-tetradecyl-N,N-dimethylammonio-3-propane sulfonate)

Reagent solution 2

10 mM Bis-Tris Methane, pH 7,5

0.05 mg/ml PAMPS

An L DL-free VLDL preparation was first added to a native sample with a low VLDL contents (16 mg/dl). 250 µl of reagent solution 1 were then added to 5 µi of this sample and for 5 minutes incubated at 37° C. Subsequently, 50 µl of reagent solution 2 were added and incubated for another 5 minutes at 37° C. Immediately after this incubation, the resulting turbidity was measured bichromatically at 505 nm (reference wavelength 700 nm).

From Table 1 it can be seen that a concentration of 0.005 and 0.01% Zwittergent is effective; i.e. VLDL interference was almost completely eliminated while a significant interference was observed beginning with 25 mg/dl of VLDL when no detergent was added.

TABLE 1

| | VLDL-Conc. | LDL-Conc. (UZ) | Zwittergent3-14(%); LDL values in mg/dl | | | | | |
|---|---|---|---|---|---|---|---|---|
| Sample | (mg/dl) | (mg/dl) | 0 | 0.0005 | 0.001 | 0.002 | 0.005 | 0.01 |
| 1 | 16 | 118 | 143 | 140 | 147 | 141 | 136 | 144 |
| 2 | 26 | 113 | 156 | 149 | 149 | 149 | 134 | 134 |
| 3 | 44 | 103 | 170 | 176 | 179 | 171 | 130 | 118 |
| 4 | 66 | 91 | 200 | 210 | 213 | 196 | 114 | 112 |
| 5 | 88 | 79 | 214 | 206 | 213 | 202 | 73 | 81 |
| | | | % recovery | | | | | |
| 1 | 16 | 118 | 121 | 118 | 125 | 120 | 115 | 122 |
| 2 | 26 | 113 | 138 | 132 | 132 | 132 | 119 | 119 |
| 3 | 44 | 103 | 165 | 171 | 174 | 166 | 126 | 115 |
| 4 | 66 | 91 | 220 | 230 | 234 | 216 | 125 | 123 |
| 5 | 88 | 79 | 271 | 261 | 270 | 256 | 92 | 102 |

EXAMPLE 2

Effect of Different Zwitterionic Detergents on VLDL Interference in a Homogeneous LDL Test Reagent solution cf. example 1

The following detergents were used in addition to Zwittergent 3-14

Zwittergent 3-08

Zwittergent 3-10

Zwittergent 3-12

Zwittergent 3-16

As described for example 1, an LDL-free VLDL preparation was added to a native sample with a low VLDL contents (16 mg/ml).

Table 2 shows that besides Zwittergent 3-14, Zwittergent 3-16 also shows a very good interference-reducing effect on the VLDL-spiked sample. Variants which contain a somewhat shorter alkyl group do not lead to an improvement in the concentrations tested.

TABLE 2

| | | | | 1. Values in mg/dl | | | |
|---|---|---|---|---|---|---|---|
| | VLDL-Conc. | LDL-Conc. (UZ) | without | Zwittergent 3-14 | Zwittergent 3-08 | | |
| Sample | (mg/dl) | (mg/dl) | Zwittergent | 0.005% | 0.0025% | 0.0050% | 0.0075% |
| 1 | 16 | 118 | 136 | 137 | 136 | 140 | 139 |
| 2 | 26 | 113 | 152 | 135 | 150 | 159 | 160 |
| 3 | 44 | 103 | 181 | 130 | 181 | 189 | 187 |
| 4 | 66 | 91 | 204 | 118 | 209 | 215 | 215 |
| 5 | 88 | 79 | 226 | 92 | 226 | 228 | 233 |
| | | | | 2. % recovery | | | |
| 1 | 16 | 118 | 116 | 116 | 115 | 119 | 118 |
| 2 | 26 | 113 | 135 | 119 | 133 | 141 | 142 |
| 3 | 44 | 103 | 176 | 126 | 176 | 184 | 182 |
| 4 | 66 | 91 | 224 | 129 | 230 | 236 | 236 |
| 5 | 88 | 79 | 287 | 117 | 286 | 289 | 294 |

| | 1. Values in mg/dl | | | | | | | | |
|---|---|---|---|---|---|---|---|---|---|
| | Zwittergent 3-10 | | | Zwittergent 3-12 | | | Zwittergent 3-16 | | |
| LDL-Conc. (UZ) (mg/dl) | 0.0025% | 0.0050% | 0.0075% | 0.0025% | 0.0050% | 0.0075% | 0.0025% | 0.0050% | 0.0075% |
| 118 | 134 | 138 | 137 | 133 | 137 | 141 | 133 | 126 | 113 |
| 113 | 156 | 145 | 156 | 150 | 159 | 165 | 140 | 132 | 106 |
| 103 | 181 | 180 | 183 | 186 | 183 | 187 | 126 | 124 | 123 |
| 91 | 207 | 209 | 207 | 207 | 213 | 214 | 125 | 126 | 123 |
| 79 | 227 | 226 | 229 | 226 | 228 | 230 | 109 | 119 | 114 |
| | | | | 2. % recovery | | | | | |
| 118 | 113 | 117 | 116 | 113 | 116 | 119 | 113 | 107 | 96 |
| 113 | 138 | 129 | 138 | 133 | 141 | 146 | 124 | 117 | 93 |
| 103 | 176 | 175 | 178 | 181 | 178 | 182 | 123 | 121 | 120 |
| 91 | 228 | 229 | 227 | 227 | 234 | 236 | 137 | 138 | 136 |
| 79 | 288 | 285 | 290 | 286 | 289 | 291 | 138 | 151 | 144 |

EXAMPLE 3

Effect of Different Zwitterionic Detergents and Detergent Mixtures on the Reduction of VLDL Interference in an LDL Test An LDL-free VLDL preparation with a VLDL contents of 64 mg/dl was tested as described in example 1. Since the preparation does not contain any LDL, the resulting LDL value must be 0 (optimal value).

| Reagent 1: | 10 mM Bis-Tris Methane, pH 7,5 0.03 mg/ml PAMPS + detergent |
|---|---|
| Reagent 2: | 10 mM Bis-Tris Methane, pH 7,5 120 mM MGCl$_2$ + detergent |

TABLE 3

| Detergent | LDL (mg/dl) |
|---|---|
| without detergent | 38.3 |
| 0.005% Zwittergent 3-14 | 1.0 |
| 0.01% Chaps | 10.1 |

TABLE 3-continued

| Detergent | LDL (mg/dl) |
|---|---|
| 0.01% Chapso | 10.0 |
| 0.01% Empigen | 13.8 |
| 0.01% Phosphatidylcholin | 11.8 |
| 0.01% Diheptadecanoyl | 10.5 |
| 0.01% Dodecyldimethylaminoxide Phosphatidylcholin | 8.2 |
| 0.1% Pluronic F68/0.01% Tween 20 | −0.6 |

EXAMPLE 4

Effect of the Concentration of Different Types of Zwittergent on the Reduction of the VLDL Interference The effect of the detergent concentrations of the zwittergent types 3-10, 3-12, and 3-14 in native samples with varying VLDL contents was tested. The LDL and VLDL target values of the samples were determined using the UZ method.

| Reagent 1: | 40 mM BIS-Tris Methane, pH 7,5 |
| | 24 mM MGCl$_2$ |
| | x% Zwittergent |
| Reagent 2: | 40 mM Bis-Tris Methane, pH 7,5 |
| | 0.15 mg/ml PAMPS |
| | x% Zwittergent |

Experimental design: cf. example 1

The results shown in Table 4 confirm that interference in samples containing up to 130 mg/dl VLDL can be completely eliminated. The use of Zwittergents with a shorter chain length x requires a higher concentration to reduce interference.

in which x is a number between 1 and 20, y a number between 0 and 8, $R^1$ is hydrogen, a cholamido group or a mono- or diglyceride group bound via phosphate residue, $R^2$ is hydrogen, a hydroxyl group or an oxyanion, an acid residue, a hydroxyalkyl sulphonic acid group or a carboxyl group, and

TABLE 4

| | Concentration measured (mg/dl) | | | | | |
|---|---|---|---|---|---|---|
| | Sample 1<br>LDL: 122 mg/dl<br>VLDL: 20 mg/dl | Sample 2<br>LDL: 153 mg/dl<br>VLDL: 35 mg/dl | Sample 3<br>LDL: 178 mg/dl<br>VLDL: 46 mg/dl | Sample 4<br>LDL: 237 mg/dl<br>VLDL: 46 mg/dl | Sample 5<br>LDL: 191 mg/dl<br>VLDL: 65 mg/dl | Sample 6<br>LDL: 182 mg/dl<br>VLDL: 134 mg/dl |
| Zwittergent 3-10 | | | | | | |
| 0.001% | 130 | 181 | 199 | 260 | 232 | 314 |
| 0.005% | 133 | 180 | 198 | 263 | 230 | 313 |
| 0.025% | 135 | 172 | 198 | 263 | 240 | 313 |
| 0.05% | 136 | 182 | 207 | 258 | 249 | 318 |
| 0.25% | 118 | 145 | 185 | 238 | 193 | 213 |
| Zwittergent 3-12 | | | | | | |
| 0.001% | 133 | 190 | 205 | 252 | 248 | 329 |
| 0.005% | 134 | 186 | 206 | 253 | 238 | 305 |
| 0.025% | 134 | 177 | 188 | 237 | 195 | 250 |
| 0.5% | 122 | 154 | 179 | 235 | 189 | 190 |
| Zwittergent 3-14 | | | | | | |
| 0.001% | 142 | 171 | 207 | 264 | 245 | 310 |
| 0.005% | 129 | 160 | 179 | 237 | 189 | 186 |
| % recovery | | | | | | |
| Zwittergent 3-10 | | | | | | |
| 0.001% | 107 | 118 | 112 | 109 | 121 | 173 |
| 0.005% | 109 | 118 | 111 | 111 | 120 | 172 |
| 0.025% | 111 | 112 | 111 | 111 | 126 | 172 |
| 0.05% | 111 | 119 | 116 | 109 | 130 | 175 |
| 0.25% | 97 | 98 | 104 | 100 | 101 | 117 |
| Zwittergent 3-12 | | | | | | |
| 0.001% | 109 | 124 | 115 | 106 | 130 | 181 |
| 0.005% | 110 | 121 | 116 | 107 | 125 | 161 |
| 0.025% | 110 | 116 | 106 | 100 | 102 | 137 |
| 0.05% | 100 | 101 | 101 | 99 | 99 | 104 |
| Zwittergent 3-14 | | | | | | |
| 0.001% | 116 | 112 | 116 | 111 | 128 | 170 |
| 0.005% | 106 | 105 | 101 | 100 | 99 | 102 |

I claim:

1. A method for detecting LDL in a sample comprising adding a buffer, at least one member selected from the group consisting of an LDL-precipitating agent and a water soluble polymeric LDL-aggregating agent and a zwitterionic detergent to said sample to form an LDL-aggregate and detecting said LDL-aggregate as indicating the presence of said LDL in said sample, said zwitterionic detergent being a compound of the formula the buffer is selected from the group consisting of sodium acetate, TRIS HCL, BIS Tris methane and MES and imidazole.

2. The method according to claim 1, wherein the LDL-precipitating agent is selected from the group consisting of dextrane sulfate, polyvinyl sulfate, and heparin and the water soluble polymeric LDL-aggregating agent is characterized as having at least one of an alkane sulfonic acid side group, an alkane phosphonic acid side group or an alkane carboxylic acid side group, and having a molecular weight of from 20,000 to 5,000,000 dalton as determined by gel permeation chromatography.

3. Method according to claim 1, wherein said x is an odd number between 11 and 17, said y is a number between 1 and 3, said $R^2$ is a sulfonic acid residue, a carboxyl residue, a hydroxy ethyl sulfonic acid residue or a hydropropylsulfonic acid residue and said $R^1$ is hydrogen, a steroid, a lecithin or a lysolecithin residue.

4. The method according to claim 1 wherein said zwitterionic detergent is selected from the group consisting of N-decyl-, N-dodecyl-, N-tetradecyl-or a N-hexadecyl-N, N-dimethylammonio-3-propane sulfonate and a corresponding derivative thereof.

5. The method according to claim 1 further comprising adding a non-ionic detergent selected from the group consisting of Pluronic F68 and Tween 220.

6. The method according to claim 1 wherein said LDL-aggregating agent is present at a concentration of 0.005 to 1.0 mg/ml and said detergent is present at a concentration of 0.001 to 1.0% (w/v). in the reaction mixture.

7. The method according to claim 1 further comprising adding the salts of 2-valent metal ions at a concentration of 0.001 to 020 mol/l.

8. The method according to claim 1 wherein the working temperature in the sample ranges between 10° and 40° C. and LDL aggregate is turbidimetrically determined.

9. The method according to claim 1 wherein the LDL is selected from the group consisting of LDL cholesterol, LDL apoprotein B and other molecular components of the LDL particles.

10. A reagent for the specific determination of LDL in the presence of other serum lipoproteins containing (1) dextrane sulfate, polyvinyl sulfate, a polymer possessing an alkane sulfonic acid, alkane phosphonic acid or alkane carboxylic acid side groups, (2) a buffer to adjust to a pH between 5 and 9, and (3) a detergent, characterized in that the polyanion has a molecular weight of 20,000 to 5,000,000 Dalton (gel permeation chromatography), the detergent is a compound of the general formula (II)

where x is a number between 1 and 20, y a number between 0 and 8, $R^1$ is hydrogen, a cholamido group or a mono- or diglyceride group bound via phosphate residue, $R^2$ is hydrogen, a hydroxyl group or an oxyanion, an acid residue, a hydroxyalkyl sulphonic acid group or a carboxyl group, and the buffer is sodium acetate, TRIS HCL, BIS Tris methane or MES and/or imidazole.

11. Reagent according to claim 10, wherein the dergent is selected from the group consisting of N-decyl-, N-dodecyl-, N-tetradecyl- or a N-hexadecyl-N,N-dimethylammonio-3-propane sulfonate and a derivative thereof.

12. Reagent according to claim 10, wherein the detergent is Pluronic F68 and/or Tween 20.

13. Reagent according to claim 10, wherein said reagent is present on or in a leaf-like carrier in an impregnated form.

14. The method according to claim 1, wherein said buffer has a pH ranging from about 5 to about 9.

* * * * *

UNITED STATES PATENT AND TRADEMARK OFFICE
CERTIFICATE OF CORRECTION

PATENT NO. : 5,804,450
DATED : September 8, 1998
INVENTOR(S) : Johann KARL

It is certified that error appears in the above-identified patent and that said Letters Patent is hereby corrected as shown below:

In Claim 3, column 11, line 2, change "hydropo" to -- hydroxypro --.

In Claim 4, column 11, line 7, change "N-tetradecyl-or" to -- N-tetradecyl- or --.

In Claim 5, column 11, line 12, change "220" to -- 20 --.

In Claim 11, column 12, line 20, change "dergent" to -- detergent --.

UNITED STATES PATENT AND TRADEMARK OFFICE
CERTIFICATE OF CORRECTION

PATENT NO. : 5,804,450
DATED : September 8, 1998
INVENTOR(S) : Johann KARL

It is certified that error appears in the above-identified patent and that said Letters Patent is hereby corrected as shown below:

In column 2, line 51, change "Stofte" to -- Stoffe --.

In column 6, line 22, change "L DL" to -- LDL --.

In column 6, line 24, change "$\mu$i" to -- $\mu$l --.

In column 6, line 57, after "solution" add -- : --.

Signed and Sealed this

Twenty-fifth Day of January, 2000

Acting Commissioner of Patents and Trademarks

UNITED STATES PATENT AND TRADEMARK OFFICE
CERTIFICATE OF CORRECTION

PATENT NO. : 5,804,450
DATED : September 8, 1998
INVENTOR(S) : Johann Karl

Figure 1:
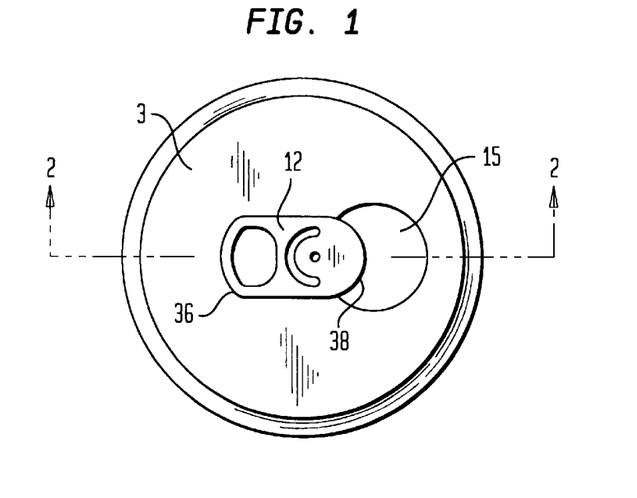
FIG. 1:
Recovery of LDL (in percent) in dependency upon the VLDL contents [mg/dl]
Figure 2:
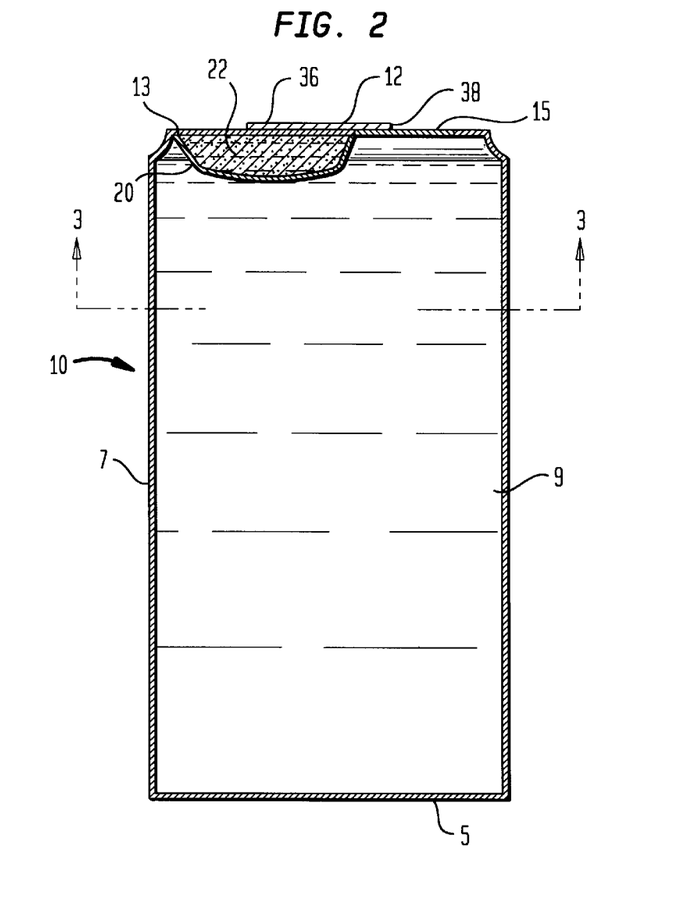
Figure 3:
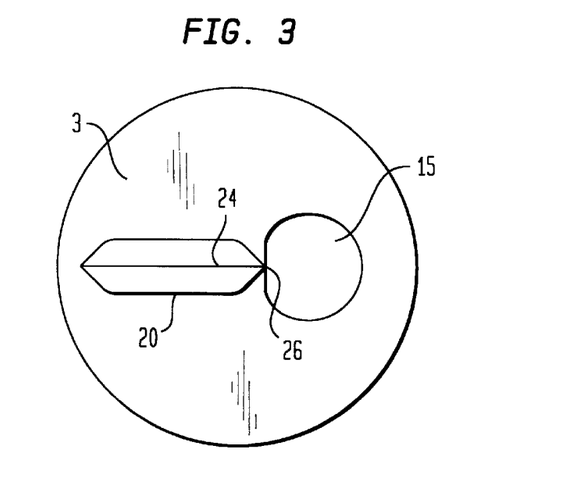
Figure 3A:
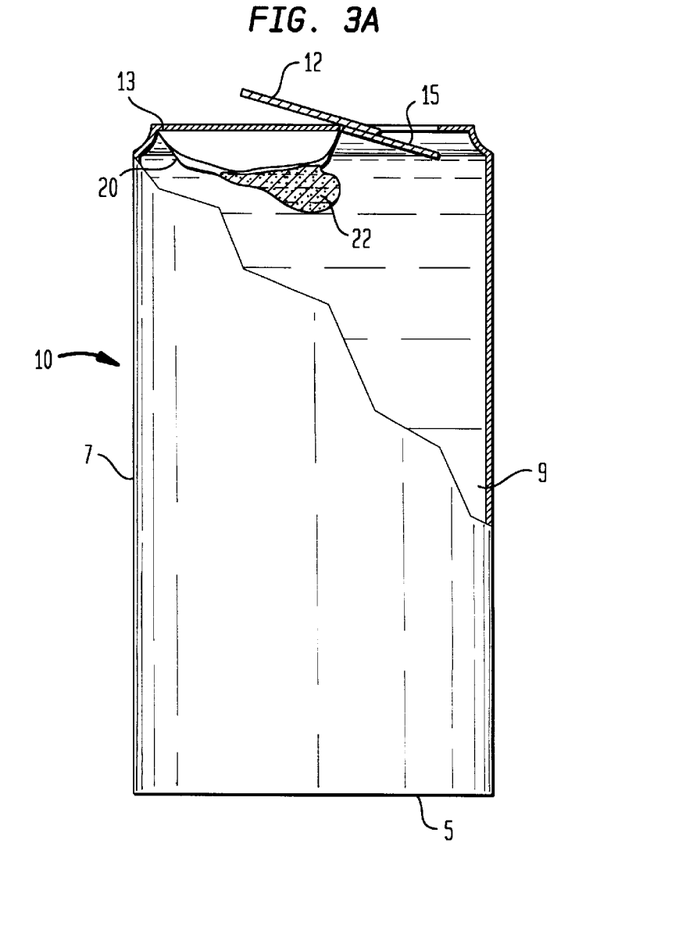
Figures 4, 5:
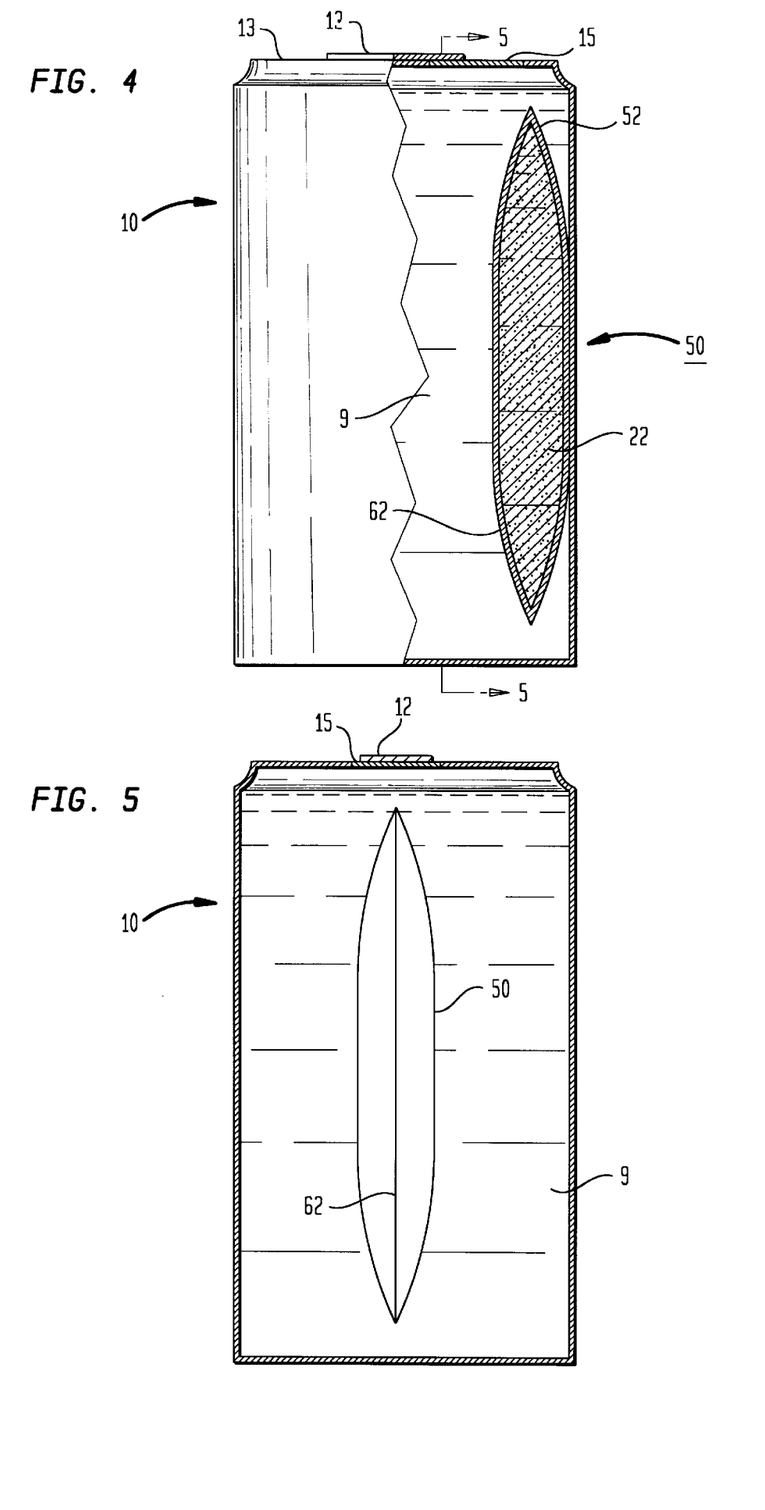

It is certified that error appears in the above-identified patent and that said Letters Patent is hereby corrected as shown below:

In column 9, line 63, insert a comma after the word "agent" to read as - - agent, - -.
In column 11, line 18, change "2-valent" to read as - - bi-valent - -.
In column 11, line 19, "020" to read as - - 0.20 - -.
Delete Figures 1-5 and insert therefore Figure 1.

Signed and Sealed this

Twenty-first Day of November, 2000

Attest:

Q. TODD DICKINSON

Attesting Officer

Director of Patents and Trademarks

UNITED STATES PATENT AND TRADEMARK OFFICE
CERTIFICATE OF CORRECTION

PATENT NO. : 5,804,450
DATED : September 8, 1998
INVENTOR(S) : Johann Karl

It is certified that error appears in the above-identified patent and that said Letters Patent is hereby corrected as shown below:

Figure 1